(12) United States Patent
Grass et al.

(10) Patent No.: US 10,769,787 B2
(45) Date of Patent: Sep. 8, 2020

(54) DEVICE FOR PROJECTING A GUIDANCE IMAGE ON A SUBJECT

(71) Applicant: KONINKLIJKE PHILIPS N.V., Eindhoven (NL)

(72) Inventors: Michael Grass, Buchholz In Der Nordheide (DE); Dirk Schäfer, Hamburg (DE); Thirukumaran Thangaraj Kanagasabapathi, Eindhoven (NL); Bernardus Hendrikus Wilhelmus Hendriks, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 16 days.

(21) Appl. No.: 16/063,920

(22) PCT Filed: Dec. 22, 2016

(86) PCT No.: PCT/EP2016/082479
§ 371 (c)(1),
(2) Date: Jun. 19, 2018

(87) PCT Pub. No.: WO2017/109130
PCT Pub. Date: Jun. 29, 2017

(65) Prior Publication Data
US 2019/0005646 A1   Jan. 3, 2019

(30) Foreign Application Priority Data
Dec. 22, 2015 (EP) .................................. 15201851

(51) Int. Cl.
*G06K 9/00* (2006.01)
*G06T 7/00* (2017.01)
(Continued)

(52) U.S. Cl.
CPC .......... *G06T 7/0014* (2013.01); *A61B 6/5247* (2013.01); *A61B 8/5261* (2013.01);
(Continued)

(58) Field of Classification Search
None
See application file for complete search history.

(56) References Cited

U.S. PATENT DOCUMENTS 6,314,311 B1 * 11/2001 Williams ............. A61B 8/0841
345/7
8,781,186 B2  7/2014 Clements
(Continued)

FOREIGN PATENT DOCUMENTS

DE   102006037778 A1   2/2008
EP        2123232 A1   11/2009
(Continued)

*Primary Examiner* — Henok Shiferaw

(57) ABSTRACT

The present invention relates to providing a projection data for providing a guidance image. In order to provide an enhanced guiding image technique for generating a guidance image of the patient's anatomy to be projected on the body surface of the patient, such that a at least a basis for a corrected guidance image for a better correlation to the patient's current motion can be provided, in particular to the patient's current breathing motion state, a device (10) for providing a projection data set is provided that comprises a storage means (12), an input interface (14), a processing unit (16) and an output interface (18). The storage means is configured to store a pre-determined basis data set representing a 3D tomographic image of a subject (20). The input interface is configured to receive reference data representing a current spatial depiction at least of a target region (22) of the subject. The processing unit is configured to register the reference data on the pre-determined basis data set. The processing unit is further configured to transform, based on the reference data and the result of the registration, the (Continued)

pre-determined basis data set resulting in a working data set representing a transformed 3D tomographic image indicating the current spatial anatomy relation at least for the target region of the subject. The processing unit is also configured to segment the working data set resulting in a projection data set representing the target region of the subject. Still further, output interface is configured to provide the projection data set for a further purpose.

12 Claims, 5 Drawing Sheets

(51) Int. Cl.
*A61B 90/00* (2016.01)
*G06T 7/11* (2017.01)
*G06T 7/33* (2017.01)
*A61B 6/00* (2006.01)
*A61B 8/08* (2006.01)
*A61B 34/20* (2016.01)
*A61B 17/00* (2006.01)

(52) U.S. Cl.
CPC ............... *A61B 90/361* (2016.02); *G06T 7/11* (2017.01); *G06T 7/337* (2017.01); *A61B 2017/00699* (2013.01); *A61B 2034/2065* (2016.02); *A61B 2090/366* (2016.02); *A61B 2090/376* (2016.02); *A61B 2090/378* (2016.02); *A61B 2090/3762* (2016.02); *A61B 2090/3764* (2016.02); *G06T 2207/10081* (2013.01)

(56) References Cited

U.S. PATENT DOCUMENTS

| | | |
|---|---|---|
| 2005/0180544 A1 | 8/2005 | Sauer |
| 2013/0069940 A1* | 3/2013 | Sun ..................... G09B 19/003 345/419 |
| 2014/0350389 A1 | 11/2014 | Powell |

FOREIGN PATENT DOCUMENTS

| | | |
|---|---|---|
| WO | 2010067281 A1 | 6/2010 |
| WO | 2013055707 A1 | 4/2013 |
| WO | 2015164402 A1 | 10/2015 |
| WO | 2015177012 A1 | 11/2015 |

\* cited by examiner

DEVICE FOR PROJECTING A GUIDANCE IMAGE ON A SUBJECT

CROSS-REFERENCE TO PRIOR APPLICATIONS

This application is the U.S. National Phase application under 35 U.S.C. § 371 of International Application No. PCT/EP2016/082479, filed on Dec. 22, 2016, which claims the benefit of European Patent Application No. 15201851.1, filed on Dec. 22, 2015. These applications are hereby incorporated by reference herein.

FIELD OF THE INVENTION

The present invention relates to a device for providing a projection data set, a system for projecting a guidance image on a subject, a method for providing a projection data set, a computer program element and a computer-readable medium.

BACKGROUND OF THE INVENTION

X-ray imaging systems may be used for various clinical procedures ranging from catheter or needle based interventions in radiology, cardiology, or oncology up to surgical procedures. For example, trans-catheter aortic valve implementation (TAVI) is a very important procedure, where a minimal invasive surgical intervention is carried out. Accordingly, a surgical entrance point and its spatial relation to the underlying anatomy of the patient, which is also referred to as the subject in the following description, is important for safe and accurate interventions. Projecting the subject's anatomy on the body surface is a technique to guide an interventional device to be inserted.

U.S. Pat. No. 6,314,311 B1 relates to a registration system for use in connection with an image guiding surgery system. It includes a medical diagnostic imaging apparatus for collecting image data from the subject. An image data processor reconstructs an image representation of the subject from the image data. An image projector depicts the image representation on the subject. However, the images of the subject are obtained prior to a planned interventional and/or surgical procedure via the medical diagnostic imaging apparatus. The images are taken at different positions and time of a respiratory cycle of the subject. The depicted image projected on the subject is then selected accordingly from the set of diagnostic images in order to bring the image in coincidence with the anatomy of the subject.

International Patent Application Publication No. WO2013/055707 A1 relates to an image-guided surgery system, which allows a surgeon to have more information available at the surgical site by performing procedure. For this purpose, a camera/projection combination unit is provided in conjunction with a medical imaging device such as MRI or CT. A multi-modality image registration system supporting an interactive overlay of potentially fused pre- and intra-operative image data is disclosed, which could support needle-based interventions.

U.S. Pat. No. 6,314,311 B1 relates to an image guidance surgery system with a registration system, which is employed to correlate an image of the subject's anatomy with the corresponding actual anatomy of the subject present within a subject support system defined in real space. For this purpose, a detection unit resolves the spatial location of emitters affixed to the patient support, such that the location of the subject thereon is tracked. Further, a rotation, translation and scaling processor of the system determines appropriate corrections to be applied to the image for the respective location of the subject and generates adjustment employed by a projector processor, such that the image being projected is depicted in a proper size and rotation on the region of interest of the subject.

U.S. Patent Application Publication No. US-2014/0350389 A1 relates to a system and a method for surgical planning and navigation. For this purpose, data representing an image of a portion of a patient's body is received. A first three-dimensional model of the portion of the patient's body is generated based on the data representing the image. A second three-dimensional model of a medical device is fitted within the first three-dimensional model at a location in proximity to the target region to create a combined three-dimensional model. Further, a two-dimensional projection of the combined three-dimensional model is created. Furthermore, the two-dimensional projection is matched to a real-time two-dimensional intraoperative image. The two-dimensional projection and the real-time two-dimensional intraoperative image can both be displaced to facilitate comparison.

SUMMARY OF THE INVENTION

There may be a need to provide an enhanced guiding image technique for generating a guidance image of the patient's anatomy to be projected on the body surface of the patient, such that a at least a basis for a corrected guidance image for a better correlation to the patient's current motion can be provided, in particular to the patient's current breathing motion state.

The object of the present invention is solved by the subject-matter of the independent claims, wherein further embodiments are incorporated in the dependent claims.

It should be noted that the following described aspects of the invention apply also for the system for providing a guidance image on a subject, the method for providing a projection data set, the computer program element and the computer-readable medium.

According to a first aspect of the present invention, a device for providing a projection data set is provided, comprising: a storage means, an input interface, a processing unit, and an output interface. The storage means is configured to store a pre-determined basis data set representing a 3D tomographic image of a subject. The input interface is configured to receive reference data representing a current spatial depiction at least of a target region of the subject. The processing unit is configured to register the reference data on the pre-determined basis data set. The processing unit is configured to transform, based on the reference data and the result of the registration, the pre-determined basis data set resulting in a working data set representing a transformed 3D tomographic image indicating the spatial anatomy relation at least for the target region of the subject. The processing unit is configured to segment the working data set resulting in a projection data set representing the target region of the subject. The output interface is configured to provide the projection data set for a further purpose.

In an example, prior to a planned interventional and/or surgical procedure, a 3D tomographic image of the subject may be determined based on a plurality of different tomographic sub-images of the subject captured with a tomographic imaging means, for example by a computer tomographic scanner (CT), a magnetic resonance imaging scanner (MRI), gamma camera, and/or other medical tomographic diagnostic imaging equipment. In particular, based on the tomographic sub-images, the 3D tomographic image of the subject may be determined by a server remote from the device.

In an example, the target region of the subject is pre-defined.

In an example, the pre-determined basis data set represents a 3D tomographic image of a target region of the subject.

In an example, the 3D tomographic image of the subject may refer to a particular motion state of the subject, preferably a particular breathing motion state of the subject.

In an example, the 3D tomographic image of the subject may refer to a particular motion state of an internal organ, in particular a heart, of the subject.

In a further example, the 3D tomographic image of the subject may refer to a particular deformation, in particular body deformation occurring during a surgical procedure, of the subject, in particular with respect to its surface and/or one of its internal organs.

In a further example, the 3D tomographic image of the subject may refer to a particular orientation, in particular surface orientation, of the subject.

In an example, the spatial depiction relates to a 2D spatial depiction or a 3D spatial depiction.

In an example, since the reference data represents a current spatial depiction at least of a target region of the subject, the reference data may at least indirectly represent the current spatial anatomy relation or depiction at least of the target region of the subject. Accordingly, the reference data may comprise the information about the current, and thus the actual breathing motion state of the subject.

In an example, the spatial depiction at least of the target region of the subject indicates a surface structure at least of the target region of the subject and/or indicates the position and/or the orientation of anatomy parts at least of the target region of the subject.

In an example, the surface at least of the target region of the subject may indicate or represent information about the position and/or orientation of anatomy parts of the subject at least at its target region.

In an example, the reference data may be formed by optical image data, X-ray image data and/or other data suitable for representing spatial depiction at least of the target region of a subject.

In a further example, the spatial depiction at least of the target region of the subject indicates a breathing motion state of the subject or another motion state of the subject.

As an effect, the reference data may provide information about the current breathing motion state of the subject and/or another motion state of the subject.

The pre-determined basis data set is transformed by means of the processing unit based on the reference data set. As a result, a working data set representing a transformed 3D tomographic image indicating the current spatial anatomy relation at least for the target region of the subject is provided.

As an effect, the 3D tomographic image can be adapted to map the current spatial anatomy relation of the subject.

In an example, the transformation may be carried out for a sub-set of the 3D tomographic image of the target region of the subject.

In an example, the transformation relates to a deformation. Further, the transformation may comprise registration.

In an example, the reference data corresponds to a smaller amount of data than the 3D tomographic image of the subject, in particular of its sub-set relating to the target region of the subject.

As an effect, the reference data preferably corresponds to a small amount of data, which may be captured with a simple imaging means. Accordingly, a respective small amount of data can be sufficient to be used to transform the 3D tomographic image, which preferably corresponding to a large amount of data.

As a further effect, the reference data can be updated during use of the device and thus may provide a basis to update the transformation of the 3D tomographic image resulting in an updated working data set as well as in an updated projection data set.

In an example, the input interface is configured to continuously receive reference data or configured to receive reference data in predefined subsequent time intervals. Thus, the pre-determined basis data set may be transformed each time after receiving new or updated reference data.

As an effect, the transformation of the predefined basis data set may be updated continuously or in subsequent time intervals, thus being able to update the projection data set accordingly.

As an effect, an enhanced representation of the projection data may be provided.

In an example, the projection data set may be used to project a guidance image on the surface of the subject.

As an effect, a precision enhanced guidance image can be projected on the surface of the subject.

According to an exemplary embodiment of the device according to the present invention, the processing unit is configured to segment the working data set, such that the resulting projection data set represents an anatomy of the target region of the subject and/or an entrance point at a surface of the target region of the subject.

In an example, the anatomy of the target region relates to a part of the anatomy of the target region of the subject.

As an effect, the projection data set can be used to project a guidance image, determined based on the projection data, on the surface of the subject to guide to a point of interest or a region of interest.

As a further effect, the projection data set may be used for a safe and accurate intervention.

According to an exemplary embodiment of the device according to the present invention, the processing unit is configured to register the reference data on the pre-determined basis data set, wherein the processing unit is configured to carry out the transformation as a deformation based on a result of the registration.

In an example, the registration may comprise establishing a relationship between the reference data and the pre-determined basis data set. This may be accomplished by identification of a plurality of points in the reference data and the pre-determined basis data set, in order to determine the relationship, in particular by defining a transformation rule, further particularly by defining a transformation matrix, between the reference data and the pre-determined basis data set, or vice versa. As a result, the transformed 3D tomographic image represented by the working data set comprises the current spatial anatomy relation at least for the target region of the subject. In case the spatial depiction represented by the reference data relates to a surface at the target region of the subject, a resulting registration rule or transformation matrix may be used to transform the whole 3D tomographic image of the subject, or at least a sub-set thereof representing the target region of the subject.

As an effect, just one pre-determined basis data set may be needed.

In an example, the transformation may relate to two sub-steps, namely the registration and the deformation based on the registration result. Further, the processing unit may be configured to carry out both sub-steps.

In a further example, the registration relates to a sub-set of the pre-determined basis data set, wherein a corresponding registration rule or transformation matrix forms the basis for the deformation of the complete pre-determined basis data set, or a sub-set thereof representing the target region of the subject.

As an effect, after receiving updated reference data, the processing unit may be configured to carry out the transformation thereupon, in order to provide an updated working data set and to provide, based thereon, an updated projection data set.

As a further effect, for updating the projection data set, the same pre-determined basis data set may be used, wherein for each update, updated reference data is employed.

According to a further exemplary embodiment of the device according to the present invention, the input interface is configured to receive updated reference data in pre-determined time intervals or continuously.

As an effect, after receiving updated reference data, an updated projection data set may be provided with an enhanced precision of the projection data, which may be used to determine a guidance image to be projected on the subject.

According to a further exemplary embodiment of the device according to the present invention, the reference data is formed by reference image data.

In an example, the reference image data relates to 2D reference image data.

In a further example, an optical imaging configuration may be used to provide the reference image data, in particular the 2D reference image data.

In a further example, the optical imaging configuration may be formed by a camera, in particular by a video camera.

As an effect, updated reference image data may be provided continuously or in predefined, in particular short, time intervals.

As a further effect, the projection data set may be updated in corresponding time intervals or in predefined time intervals.

As a further effect, an enhanced precision of the projection data can be provided.

In an example, the reference image data is used to be registered on the pre-determined basis data set. The resulting transformation rule or transformation matrix may be used to transform, in particular deform, the complete pre-determined basis data set or a sub-set thereof relating to the target region of the subject.

In a further example, the optical imaging configuration is integrated or coupled to an X-ray imaging system. Accordingly, a registration may be simplified.

According to a further exemplary embodiment of the device according to the present invention, the reference data is formed by tomographical reference image data.

In an example, the tomographical reference image data relates to a 2D tomographical reference image data.

As an effect, a small amount of data corresponding to the tomographic reference image data may be used to transform the pre-determined basis data set. This may result in a reduced processing effort, which allows to update the projection data set in short time intervals.

In an example, an X-ray imaging configuration may be used for providing the tomographical reference data.

As an effect, an enhanced transformation, and in particular an enhanced registration, may be provided.

According to a further exemplary embodiment of the device according to the present invention, the storage means is configured to store a plurality of image data sets each representing a corresponding spatial depiction at least of the target region of the subject, wherein the processing unit is configured to select, based on the reference data, one of the plurality of image data sets as a reference image data set, and wherein the processing unit is configured to transform, based on the reference image data set, the pre-determined basis data set resulting in the working data set representing the transformed 3D tomographical image indicating the current spatial anatomy relation at least for the target region of the subject. In an example, the plurality of image data sets may relate to a plurality of pre-determined image data sets. Accordingly, the pre-determined image data sets may be stored by the storing means of the device.

In an example, the pre-determined image data sets may be captured prior to a planned interventional and/or surgical procedure.

In an example, each of the image data sets is formed by optical image data and/or tomographical image data.

In an example, the image data sets may relate to different breathing motion states of the subject and/or to different motion states of the subject, in particular to different positions and/or orientations of the subject.

In an example, the processing unit is configured to select one of the plurality of image data sets, which provides the best coincidence with the reference data.

As an effect, based on the reference data, one of the plurality of image data sets may be selected, which corresponds to the current motion state, in particular breathing motion state, of the subject and/or to the current orientation or position of the subject.

In particular with respect to the above noted further examples to which the 3D tomographic image of the subject may refer to, one of the plurality of image data sets may be selected, which corresponds to a particular motion state of an internal organ, in particular a heart, of the subject, or to a particular deformation, in particular body deformation occurring during a surgical procedure, of the subject, preferably with respect to its surface and/or one of its internal organs, or to a particular orientation, in particular surface orientation, of the subject.

As a further effect, the amount of the reference data may be reduced, since less data may be needed to select one of the plurality of image data sets.

As an effect, the processing unit may be configured to perform a cascade of steps, wherein the selection step is carried out before the transformation step. This cascade may reduce the necessary data amount of the reference data in order to update the projection data set.

According to second aspect of the present invention, a system for projecting a guidance image on a subject is provided, comprising: a detecting means, an optical projecting means, and a device according as described above. The detecting means is configured to detect the subject resulting in reference data representing a current spatial depiction at least of a target region of the subject. The detecting means is connected to the input interface of the device for transferring the reference data. The output interface of the device is connected to the optical projecting means for transferring the projection data set. The optical projecting means is configured to project, based on the projection data set, a guidance image on the subject.

It is understood that, without repeating here all the examples, effects and explanations provided with reference to the device, the system of the present invention is intended to preferably comprise analogous exemplary features and effects as described with reference to the device. Thus, all the above explained examples, effects and/or explanations, although firstly provided with reference to the device, are also to be intended preferably being implemented by the system.

As an effect, anatomy information of the subject, and in particular an entry point for an interventional and/or surgical procedure, may be projected on the surface of the subject, wherein the reference data provided by the detecting means may be used to update the projection data set and therefore to update the guidance image to be projected on the subject.

According to an exemplary embodiment of the system according to the present invention, the detecting means comprises at least one optical camera arrangement.

In an example, the detecting means comprises a camera, in particular video camera, as at least one optical camera arrangement.

In a further example, the detection means comprises a plurality of cameras, in particular video cameras, as at least one optical camera arrangement. The detection means may be configured to provide image data composed of the image data provided by the plurality of cameras. Thus, the detection mean is preferably configured to provide a 3D image or a 3D video stream composed of the sub-images or sub-video streams, respectively, of the plurality of cameras.

As an effect, the reference data may be provided by a cost-effective camera or camera arrangement.

As a further effect, the reference data may have a limited data amount.

As a further effect, the reference data can be updated continuously and/or in predefined time intervals.

According to a further exemplary embodiment of the system according to the present invention, the detecting means comprises at least one X-ray detection arrangement.

As an effect, the reference data may represent a current spatial anatomy depiction at least of the target region of the subject.

As an effect, a registration of the reference data on the pre-determined basis data set may be simplified.

As a further effect, an enhanced precision of the registration and/or the transformation may be provided.

According to a further exemplary embodiment of the system according to the present invention, the detecting means comprises at least one ultrasonic detection arrangement.

As an effect, the at least one ultrasonic detection arrangement may be a cost-effective embodiment of the detecting means.

In an example, the at least one ultrasonic detection arrangement may be configured to provide reference data representing a current spatial anatomy depiction at least of the target region of the subject.

As an effect, a registration precision of the reference data on the pre-determined basis data set may be enhanced.

As a further effect, the transformation may be enhanced.

According to third aspect of the present invention, a method for providing a projection data set is provided, comprising the following steps:

a) receiving reference data representing a current spatial depiction at least of a target region of the subject;

b) transforming, based on the reference data, a pre-determined basis data set, which represents a 3D tomographic image of the subject, resulting in a working image data set representing a transformed 3D tomographic image indicating the current spatial anatomy relation at least for the target region of the subject;

c) segmenting the working data set resulting in a projection data set representing the target region of the subject; and d) providing the projection data set for a further purpose.

It is understood that, without repeating here all the examples, effects and explanations provided with reference to the device or the system of the present invention, the method of the present invention is preferably intended to be configured to carry out analogous method steps. Thus, all the above explained examples, effects and explanations, although firstly provided with reference to the device or the system, are preferably also to be intended to provide analogous effects with respect to the method according to the present invention.

According to a fourth aspect of the present invention, a computer program element for controlling a device or system as described above, which, when being executed by a processing unit, is adapted to perform the method steps as described above.

According to a fifth aspect of the present invention, a computer-readable medium having stored the program element as described above is provided.

According to a further aspect of the present invention, a device and a method for providing a projection data set and a system for providing a guidance image is provided. Prior to a planned interventional and/or surgical procedure, tomographical images may be captured of a patient, in particular of a target region of a patient. The tomographical images may be used to determine, in particular by registration, a 3D tomographical image of the patient, in particular of a target region of the patient. Based on this 3D tomographical image, a pre-determined basis data set can be determined. The pre-determined basis data set represents the patient, in particular the target region of the patient, at a particular breathing motion state. In practice, the patient is breathing during an interventional and/or surgical procedure. In order to use the pre-determined basis data set for determining an anatomic structure to be projected on the surface of the patient, it is suggested to use an imaging means, in particular an optical or X-ray imaging means, which is configured to provide optical or X-ray images of a current breathing motion state of the patient. The detecting means is configured to provide reference data representing the optical or X-ray image of the patient at its current breathing motion state. The reference data can be updated continuously or in pre-determined time intervals. Further, the reference data is registered on the pre-determined basis data set such that a corresponding registration rule, in particular a transformation matrix, for the registration can be applied to the complete pre-determined basis data set, or in particular to a sub-set referring to the target region of the patient. As a result, a working data set can be provided, which is deformed by applying the registration rule or the transformation matrix to the pre-determined basis data set, or its sub-set. The working data set therefore corresponds to the current spatial anatomy of the patient, thus corresponding to the current breathing motion state of the patient. The working data set therefore provides a basis with enhanced precision for determining, in particular by selecting, a projection data set, which forms the basis for determining a guidance image, which can be projected on the surface of the patient in order to guide to a point of interest, in particular to an entrance point for the surgical procedure, or to project an anatomy road map. According to an embodiment of the further aspect of the present invention, prior to the planned interventional and/or surgical procedure, a plurality of image data sets may be generated, wherein each image data set corresponds to an image, in particular a two-dimensional optical image or a two-dimensional X-ray image, of the target region of the patient. The image data sets may relate to different breathing motion states, different orientations and/or different positions of the patient. Thus, the image data set may comprise information about the patient at different breathing motion states, its orientations and/or its positions. Thus, when carrying out the interventional and/or surgical procedure, an optical image, in particular provided via a video camera, may be used to select one of the image data sets, which has the highest similarity or coincidence with the current camera image. The camera image may have a small amount of data. Thus, the camera image may be used to select the best image data set, which has a higher accuracy with respect to the anatomy of the patient, in particular at its target region. The selected image data set may be used thereafter to be registered on the pre-determined basis data set, in order to carry out the above explained transformation or deformation. As an effect, a simple video camera may be used to initiate the transformation of the pre-determined basis data set with enhanced precision, in order to provide an enhanced projection data set and/or an enhanced guidance image. For updating the projection data set and/or the guidance image, just one new camera image is needed and to be processed in order to transform the pre-determined basis data set. As a further result, a limited processing power is needed during the interventional and/or surgical procedure for providing an enhanced projection data set and/or an enhanced guidance image.

BRIEF DESCRIPTION OF THE DRAWINGS

Exemplary embodiments of the invention will be described in the following with reference to the following drawings.

DETAILED DESCRIPTION OF THE EMBODIMENTS

Figure 1:
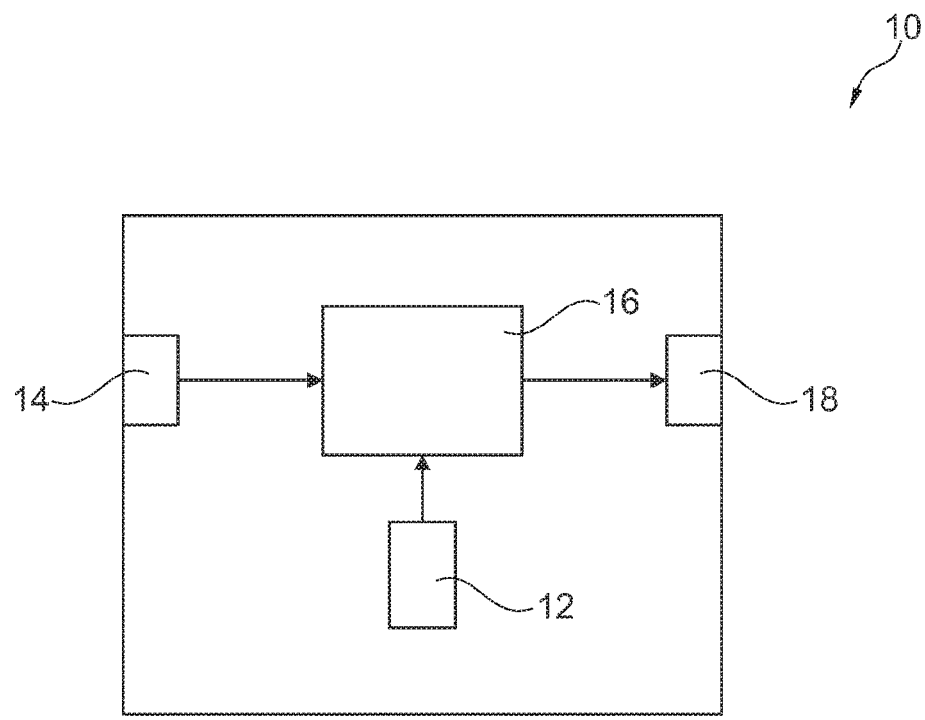
FIG. 1 schematically illustrates an example of the device according to the present invention.

FIG. 1 schematically shows an example of the device 10 according to the present invention for providing a projection data set. The device 10 comprises a storage means 12, an input interface 14, a processing unit 16 and an output interface 18. The storage means 12 is configured to store a pre-determined basis data set representing a 3D tomographic image of a subject 20 (schematically shown in FIG. 2). The input interface 14 is configured to receive reference data representing a current spatial depiction at least of a target region 22 of the subject 20. The processing unit 16 is configured to transform, based on the reference data, the pre-determined basis data set resulting in a working data set representing a transformed 3D tomographic image indicating the current spatial anatomy relation at least for the target region 22 of the subject 20. The processing unit 16 is configured to segment the working data set resulting in a projection data set representing the target region 22 of the subject 20. The output interface 18 is configured to provide the projection data set for a further purpose.

In an example, the device 10 is configured as a standalone device. Alternatively, the device 10 may be integrated in another device, apparatus or system.

In case the device 10 is configured as a standalone device, the device 10 may be connected with its input interface 14 to an X-ray imaging system, in particular to a C-arm X-ray imaging system, for transferring the reference data.

Figure 2:
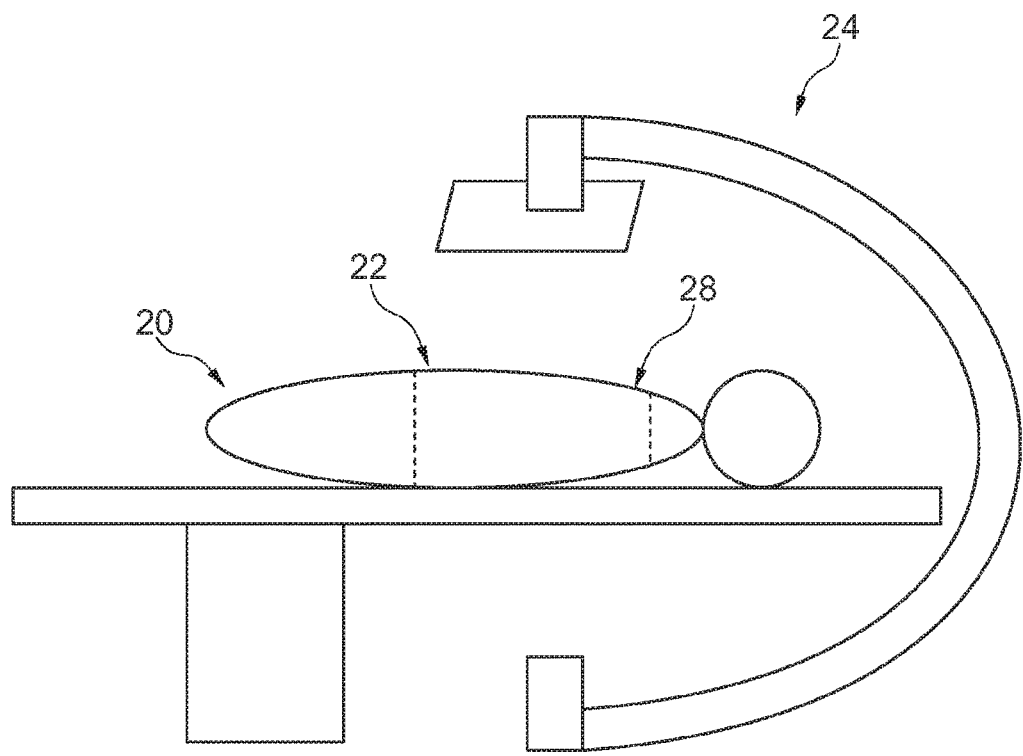
FIG. 2 schematically illustrates an example of an X-ray imaging system.

FIG. 2 schematically shows an example of an X-ray imaging system, in particular configured as a C-arm X-ray imaging system 24.

The storage means 12 of the device 10 is configured to store a pre-determined basis data set representing a 3D tomographic image of the subject 20. The X-ray imaging system 24 may be configured to capture tomographic images of the subject 20, in particular of its target region 22. These tomographic images may be used to determine a 3D tomographic image of the subject 20, in particular by using a registration algorithm.

In an example, another X-ray imaging system may be used to capture the tomographic images of the subject 20, in particular of its target region 22.

In an example, the 3D tomographic image of the subject 20, in particular of its target region 22, relates to a certain breathing motion state of the subject 20. However, the 3D tomographic image may comprise a high resolution.

In an example, the 3D tomographic image is generated and/or stored prior to a planned interventional and/or surgical procedure to be carried out at the subject 20.

During an interventional and/or surgical procedure, the subject 20, which is a human patient, has a breathing cycle and/or other biological cycles, which may cause a change of the anatomy of the subject 20 with respect to its anatomy.

In order to compensate a motion of the subject 20 and/or to compensate a change of the orientation anatomy of the subject 20, in particular caused by the breathing cycle of the subject 20, the present invention suggests transforming the pre-determined basis data set. The transformation is supposed to be based on the reference data.

The input interface 14 of the device 10 is configured to receive the reference data representing a current spatial depiction at least of the target region 22 of the subject 20.

In an example, the reference data may relate to optical image data, X-ray imaging device or other data suitable for representing the spatial depiction at least of the target region 22 of the subject 20.

As an effect, the reference data comprises information about the current anatomy structure at least of the target region 22 of the subject, of the orientation at least of the target region 22 of the subject and/or of a spatial anatomy relation of the organs at least of a target region 22 of the subject 20, wherein the anatomy relation may be determined based on the mentioned structure and/or orientation.

In an example, the reference data corresponds to a smaller amount of data than the pre-determined basis data set.

As an effect, the reference data can be updated during the interventional and/or surgical procedure, for example continuously or in predefined time intervals.

In an example, the input interface 14 is configured to receive the reference data and to provide the reference data to the processing unit 16. Further, the processing unit 16 may be configured to receive the pre-determined basis data set from the storage means 12.

The processing unit 16 is configured to transform, based on the reference data, the pre-determined basis data set resulting in a working data set representing a transformed 3D tomographic image. In particular, the pre-determined basis data set is deformed on the basis of the reference data. Since the reference data preferably comprises the information about the current spatial depiction, and in particular about a spatial anatomy relation, at least of the target region 22 of the subject 20, the transformation can be carried out, such that the working data set represents the transformed 3D tomographic image indicating the current spatial anatomy relation at least for the target region 22 of the subject 20.

As a result, the transformed 3D tomographic image may comprise an enhanced precision with respect to the actual anatomy relation at least of the target region 22 of the subject 20.

In case the reference data is updated in predefined time intervals, a motion of the subject 20, in particular of its target region 22, may be compensated by updating the working data set representing the transformed 3D tomographic image.

The processing unit 16 is further configured to segment the working data set resulting in a projection data set representing the target region 22 of the subject 20.

In an example, the segmentation of the working data set refers to a selection or filtering of the working data set resulting in the projection data set.

As an effect, the projection data set may be represented by a sub-set of the working data set.

In an example, the segmentation of the working data set is carried out, such that the projection data set represents a selected anatomy structure, a surface entrance point and/or an anatomy roadmap at the target region 22 of the subject 20. In case the selected anatomy correspond to an entrance point at the surface at the target region 22 of the subject 20 and/or to an anatomy road map from the entrance point to a target point at the anatomy of the subject 20, an enhanced guidance for interventional procedure can be provided.

The output interface 18 is configured to provide the projection data set for a further purpose.

In case the reference data is updated, a subsequent transformation of the pre-determined basis data set may be carried out by the processing unit 16. Further, a segmentation of the corresponding updated working data set may be carried out by the processing unit 16 resulting in an updated projection data set, which can be provided by the output interface 18 for the further purpose.

As an effect, after receiving an updated reference data set, the device 10 may be configured to provide an updated projection data set. As a result, an enhanced precision of the projection data set may be provided by receiving updated reference data.

As explained above, the reference data may correspond to a small amount of data, such that generating this reference data, in particular by optical image data, may be provided with reasonable effort. The pre-determined basis data set representing a 3D tomographic image at least of the target region 22 of the subject 20 is not needed to be updated, but could be pre-determined once, in particular prior to the planned interventional and/or surgical procedure.

In an example, the processing unit 16 of the device 10 is configured to segment the working data set, such that the resulting projecting data represents an anatomy of the target region 22 of the subject and/or an entrance point at the target region 22 of the subject 20.

As an effect, the projection data set may be used to determine a guidance image 26 to be projected on the surface 28 of the subject 20, in particular at its target region 22, to guide to a region of interest or a point of interest.

In an example, the processing unit 16 of the device 10 is configured to register the reference data on the pre-determined basis data set, wherein the processing unit 16 is configured to carry out the transformation, in particular as a deformation, based on a result of the registration.

In an example, the processing unit 16 may be configured to carry out a registration step for registration of the reference data on the pre-determined basis data set.

In a further example, the transformation may relate to two sub-steps, namely the registration and the deformation based on the registration result, wherein the processing unit 16 is preferably configured to carry out the sub-steps.

In an example, the result of the registration may relate to a registration rule or a registration transformation matrix. The transformation rule and/or the transformation matrix may be used to deform the complete pre-determined basis data set or a sub-set thereof relating to the target region 22 of the subject 20.

As an effect, just one pre-determined basis data set may be needed to carry out the transformation, wherein updated reference data may be used, in particular received at pre-defined time intervals.

As a further effect, the processing power can be reduced, since for the transformation, the same pre-determined basis data set, stored in the storing means 12, may be used. Thus, is not needed to determine 3D tomographic image for each transformation, but can be determined prior to the planned interventional and/or surgical procedure.

In an example, the input interface 14 of the device 10 is configured to receive updated reference data in pre-determined time intervals or continuously.

As an effect, the previously explained update may be carried out by means of the processing unit 16 in order to provide via the output interface 18 an updated projection data set.

In the following passages, an exemplary embodiment of the system 30 according to an example of the present invention is described with reference to FIG. 3. It is to be noted that, without repeating all the following examples, effects and advantages with reference to the system may also provide analogous examples, effects and/or advantages with reference to the device. Thus, the following passages with respect to the system are preferably also intended also being implemented, where suitable, for the device 10.

Figure 3:
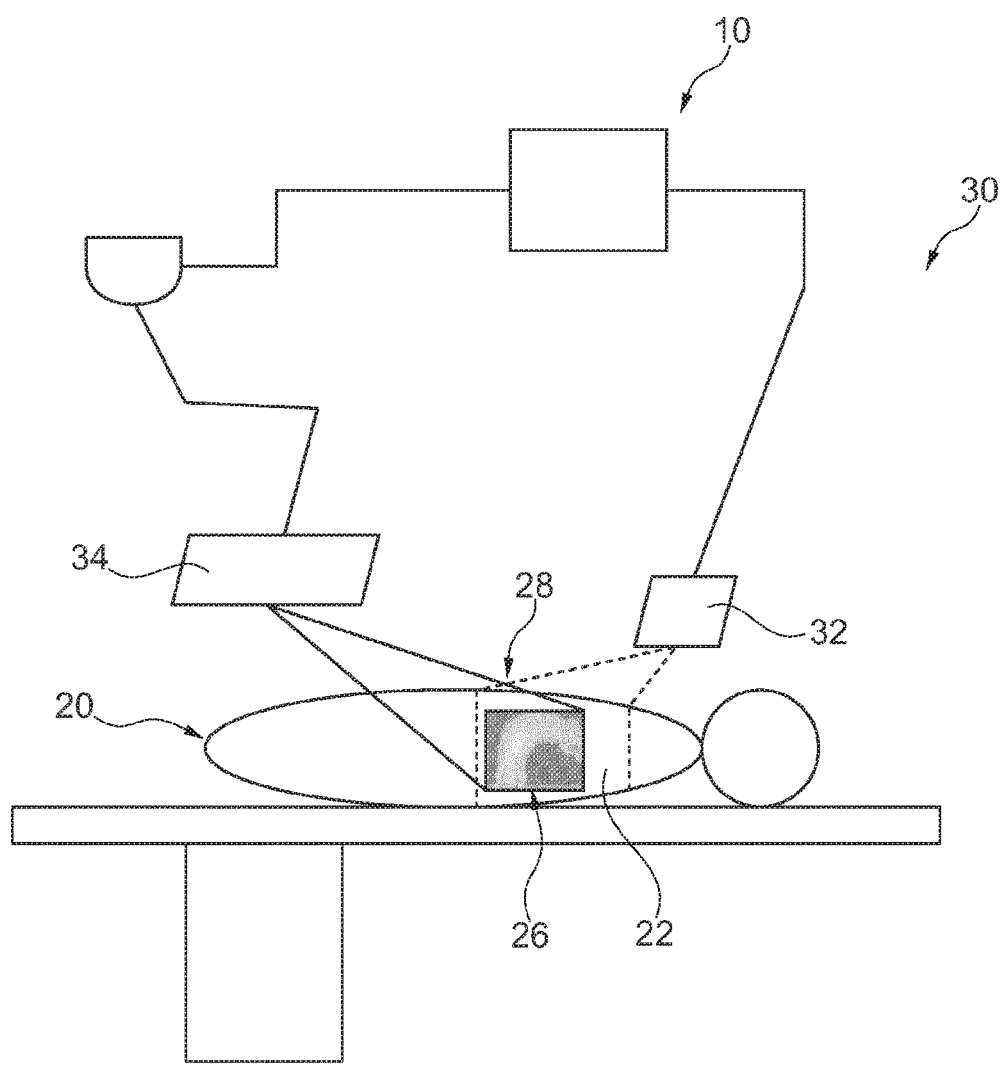
FIG. 3 schematically illustrates an example of the system according to an exemplary embodiment of the present invention.

In FIG. 3, an example of the system 30 for projecting a guidance image 26 on a subject 20 is schematically shown. The system 30 comprises a detecting means 32, an optical projection means 34 and a device 10 according to the present invention. The detecting means 32 is configured to detect the subject 20 resulting in reference data representing a current spatial depiction at least of a target region 22 of the subject 20. The detecting means 32 is connected to the input interface 14 of the device 10 for transferring the reference data. The output interface of the device 10 is connected to the optical projection means 34 for transferring the projection data set. The optical projection means is configured to project, based on the projection data set, a guidance image 26 on the subject 20.

As a result, the projecting means 32 may provide, in particular continuously or in pre-defined time intervals, reference data to the device 10. The device 10 is configured to provide the projection data set, in particular updated with each updated reference data set. The projection data set provided by the device 10 may be transferred to the projecting means 34. Since the projection data set may be updated, a motion compensation of the subject 20 may be performed. Thus, the guidance image 26 projected on the subject 20, in particular at its target region 22, preferably correspond to the current anatomy of the subject, thus can represent a motion compensated guidance image.

In an example, the guidance image may represent or indicate a surgical entrance point and/or an anatomy structure, in particular an anatomic road map, such that a safe and accurate intervention may be carried out.

In a further example, the guidance image may indicate an ascending aorta, a left atrium and/or a left atrial appendage. Thus, the processing unit 16 may be configured to segment the working data set, such that the projection data relates to the aforementioned points or region of interest.

In an example, the reference data is formed by reference image data.

In an example, the detecting means 32 of the system 30 comprises at least one optical camera arrangement. In particular, an optical camera arrangement may be formed by an optical camera or a video camera. Thus, the detecting means may be configured to provide reference image data representing an image, which may be captured by the optical camera arrangement.

In a further example, the reference image data relates to 2D reference image data. This 2D reference image data may represent an optical image, which can be captured by the optical camera arrangement.

As an effect, a cost-effective detecting means may be used for providing the reference data to the device 10. Since the storage means 12 of the device 10 is configured to store the pre-determined basis data set, a respective transformation of the pre-determined basis data set can be carried out after receiving the reference image data, in particular the 2D reference image data, such that an updated projection data set can be provided by the device 10. Correspondingly, in case the subject 20, in particular at its target region 22, has carried out a motion, the updated and thus motion compensated guidance image can be projected by the optical projection means 34 at the surface 28 of the subject 20, in particular at its target region 22.

Figure 4:
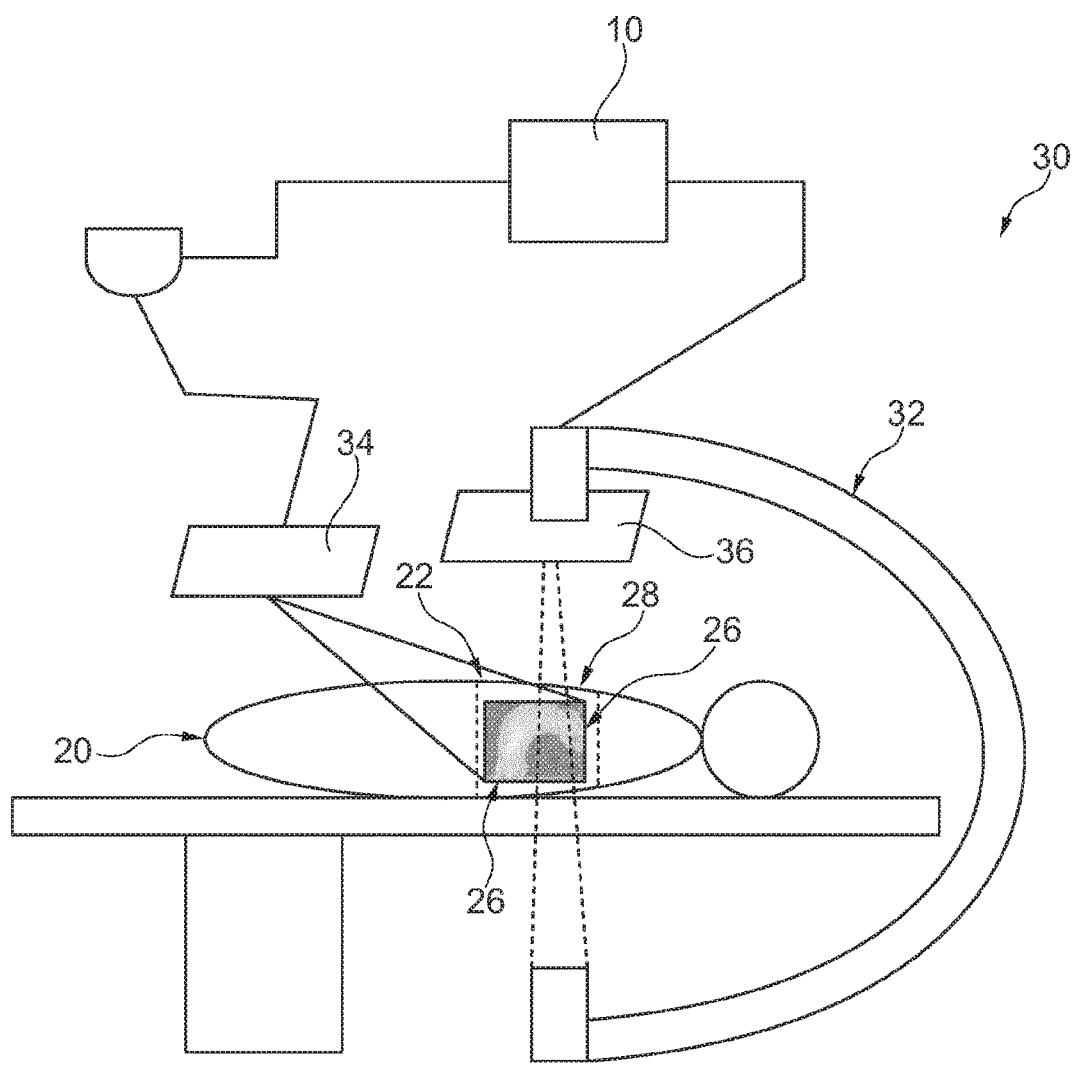
FIG. 4 schematically illustrates an example of the system according to a further exemplary embodiment of the present invention.

In FIG. 4, a further exemplary embodiment of the system 30 is schematically shown. The system 30 basically corresponds to the system 30 explained with reference to FIG. 3. However, the detecting means 32 differs with respect to the detecting means 32 described with reference to FIG. 3. The detecting means 32 shown in FIG. 4 is configured to comprise at least one X-ray detection arrangement 36. The X-ray detection arrangement 36 may be formed by a C-arm X-ray detection means.

In an example, the X-ray detection arrangement 36 may be used to acquire a set of tomographic images at least of the target region 22 of the subject 20. The set of tomographic images may be used to determine the 3D tomographic image, which is represented by the pre-determined basis data set stored in the storage means 12 of the device 10. Alternatively, the tomographic images at least of the target region 22 of the subject 20 may be captured by another X-ray detecting means.

The X-ray detection arrangement 36 shown in FIG. 4 may be configured to provide tomographical reference image data representing at least the target region 22 of the subject 20.

In an example, the reference data may be formed by the tomographical reference image data. Thus, the reference data may represent a current spatial anatomy depiction at least of the target region 22 of the subject 20. Providing this reference data to the device 10, in particular as an update, allows to calculate an updated projection data set, which provides the basis to project an updated guidance image 26 on the subject 20, in particular at its target region 22.

Using an X-ray detection arrangement 36 as a detecting means 32 may provide the advantage that a simplified and/or enhanced registration of the reference data on the pre-determined basis data set can be performed by the processing unit 16 of the device 10. Thus, an enhanced motion compensation may be provided for projecting the guidance image on the subject 20, in particular at its target region 22.

In a further example of the device 10, the storage means 12 is configured to store a plurality of image data sets each representing a corresponding spatial depiction at least of the target region 22 of the subject 20, wherein the processing unit 16 is configured to select, based on the reference data, one of the plurality of image data sets as the reference image data set, and wherein the processing unit 16 is configured to transform, based on the reference image data set, the pre-determined basis data set resulting in the working data set representing the transformed 3D tomographic image corresponding to the current spatial anatomy relation at least for the target region 22 of the subject 20.

In an example, an optical camera or an optical imaging means may be used to capture a plurality of images of the subject 20, in particular of its target region 22, wherein the plurality of images correspond to different orientations, positions and/or breathing motion states of the subject 20. These images may be captured prior to the planned interventional and/or surgical procedure. Thus, the plurality of image data sets may represent the aforementioned images as spatial depictions at least of the target region 22 of the subject 20. In an example, in case the reference data is provided, one of the plurality of image data sets can be selected by the processing unit 16. In particular, the reference data provided by the X-ray detection arrangement 36 shown in FIG. 4 or the optical camera arrangement 32 shown in FIG. 3 may be used to select one of the image data sets. The transformation is thereafter carried out by the processing unit 16 based on the reference image data set, which has been previously selected. Thus, a processing effort, in particular a corresponding processing power needed, may be reduced, since the image data sets may be pre-determined and may comprise already the information about different orientations, positions and/or breathing motion states of the subject 20, in particular of its target region 22.

According to a further example of the system 30, the detecting means 32 comprises at least one ultrasonic detection arrangement.

As an effect, the ultrasonic detection arrangement may be configured to provide the reference data.

As a further effect, an ultrasonic detection arrangement may comprise a small size and is therefore preferably configured to be arranged close to the subject 20, in particular to its target region 22.

Figure 5:
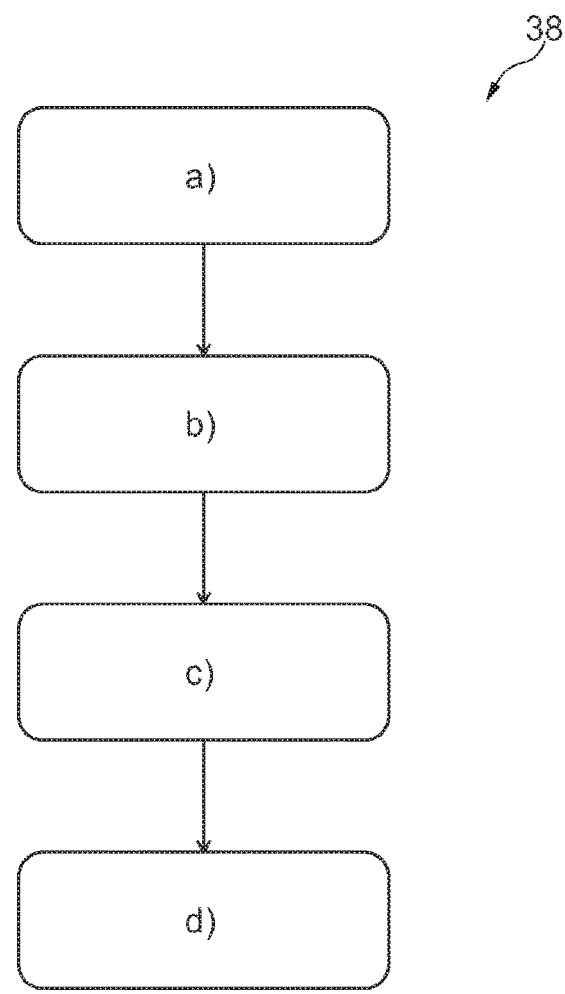
FIG. 5 schematically illustrates an example of the method according to the present invention.

In FIG. 5, an example of the method 38 according to the present invention for providing a projection data set is provided, comprising the following steps:

In a first step a), reference data representing a current spatial depiction at least of a target region 22 of a subject 20 is received.

In a step b), a pre-determined basis data set, which represents a 3D tomographic image of the subject 20, is transformed based on the reference data resulting in a working data set representing a transformed 3D tomographic image indicating the current spatial anatomy relation at least for the target region 22 of the subject 20.

In step c), the working data set is segmented resulting in a projection data set representing the target region 22 of the subject 20.

In step d), the projection data set is provided for a further purpose.

Without repeating here all the features, examples and effects provided with reference to the device 10 and/or the system 30, it is to be understood that analogous example, features and effects may also be adapted for the method 38 described above. Thus, all the features, examples and explanations, although firstly provided with reference to the device 10 and/or the system 30, are also to be intended as being implemented by the method 38 in an analogous manner.

According to a further example of the present invention, a computer program element is provided, which, when being executed by a processing unit, is adapted to carry out the method described above.

According to a further example of the present invention, a computer-readable medium having stored thereon the computer program element is provided, which, when being executed by the processing unit, is adapted to carry out the method as described above.

The computer program element might be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a processing unit. The data processor may thus be equipped to carry out the method of the invention.

It has to be noted that embodiments of the invention are described with reference to different subject matters. In particular, some embodiments are described with reference to a device whereas other embodiments are described with reference to the method. However, a person skilled in the art will gather from the above that, unless otherwise notified, in addition to any combination of features belonging to one subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A detecting means or other units may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for projecting a guidance image on a subject, comprising:
   a storage medium having stored therein a pre-determined basis data set representing a 3D tomographic image of a subject;
   an input for receiving reference data representing a current spatial depiction at least of a target region of the subject;
   a processor coupled to said storage to receive the pre-determined basis data set representing the 3D tomographic image of the subject, and to said input to receive the reference data representing the current spatial depiction at least of the target region of the subject, said processor being configured to:
   register the reference data on the pre-determined basis data set,
   transform, based on the reference data and the result of the registration, the pre-determined basis data set resulting in a working data set representing a transformed 3D tomographic image indicating the current spatial anatomy relation at least for the target region of the subject, and
   segment the working data set resulting in a projection data set representing the target region of the subject;
   an output coupled to the processor to provide the projection data set; and
   an optical projector coupled to the output to project the projection data set as a guidance image on the subject,
   wherein the processor is configured to segment the working data set, such that the resulting projection data set represents an entrance point at a surface of the subject.

2. The device as claimed in claim 1, wherein the processor is configured to segment the working data set, such that the resulting projection data set represents an anatomy of the target region of the subject and/or an entrance point at a surface of the target region of the subject.

3. The device as claimed in claim 1, wherein the input receives updated reference data in predefined time intervals or continuously.

4. The device as claimed in claim 1, wherein the reference data is formed by reference image data.

5. The device as claimed in claim 1, wherein the reference data is formed by tomographical reference image data.

6. The device as claimed in claim 1, wherein the storage medium stores a plurality of image data sets each representing a corresponding spatial depiction at least of the target region of the subject;
   wherein the processor is configured to select, based on the reference data, one of the plurality of image data sets as a reference image data set; and
   wherein the processor is configured to transform, based on the reference image data set, the pre-determined basis data set resulting in the working data set representing the transformed 3D tomographic image indicating the current spatial anatomy relation at least for the target region of the subject.

7. A system for projecting a guidance image on a subject, comprising:
   an imaging device; and
   the device for projecting a guidance image on a subject as claimed in claim 1;
   wherein the imaging device detects the subject and generates the reference data representing a current spatial depiction at least of a target region of the subject for application to the input of the device for projecting a guidance image on a subject, and
   wherein the processor is configured to segment the working data set, such that the resulting projection data set represents an entrance point at a surface of the subject.

8. The system as claimed in claim 7, wherein the imaging device comprises at least one optical camera arrangement.

9. The system as claimed in claim 7, wherein the imaging device comprises at least one X-ray detection arrangement.

10. The system as claimed in claim 7, wherein the imaging device comprises at least one ultrasonic detection arrangement.

11. A method for projecting a guidance image on a subject, comprising the following steps:
   a) receiving reference data representing a current spatial depiction at least of a target region of a subject;
   b) transforming, based in the reference data, a pre-determined basis data set, which represents a 3D tomographic image of the subject, resulting in a working data set representing a transformed 3D tomographic image indicating the current spatial anatomy relation at least for the target region of the subject;
   c) segmenting the working data set resulting in a projection data set representing the target region of the subject; and
   d) projecting the projection data set as a guidance image on the subject,
      wherein the working data set is segmented such that the resulting projection data set represents an entrance point at a surface of the subject.

12. A non-transitory computer-readable storage medium having stored a computer program element comprising instructions for controlling an apparatus, which, when being executed by a processor, is adapted to cause the processor and the apparatus to perform the method steps of claim 11.

* * * * *